Figure 1:
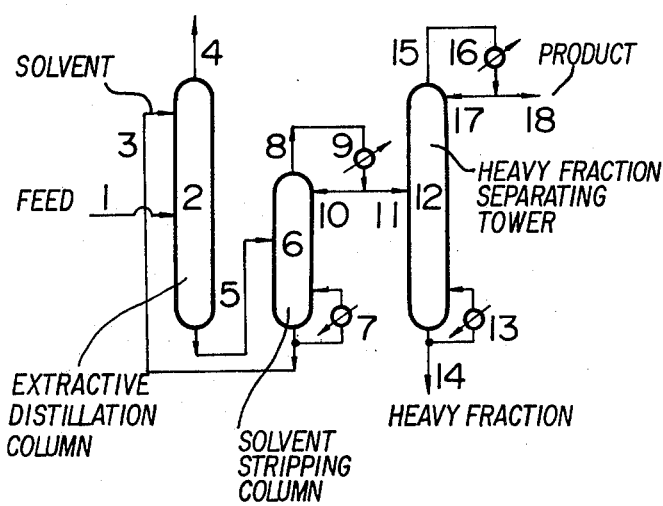

United States Patent [19]

Arakawa et al.

[11] 4,401,515

[45] Aug. 30, 1983

[54] PROCESS FOR PRODUCING 1,3-BUTADIENE OR 2-METHYL-1,3-BUTADIENE HAVING HIGH PURITY

[75] Inventors: Masatoshi Arakawa; Kazuyoshi Nakazawa, both of Yokkaichi, Japan

[73] Assignee: Japan Synthetic Rubber Co., Ltd., Tokyo, Japan

[21] Appl. No.: 242,676

[22] Filed: Mar. 11, 1981

[30] Foreign Application Priority Data

Mar. 15, 1980 [JP] Japan ................. 55-32161

[51] Int. Cl.³ .................. B01D 3/40; C07C 7/08
[52] U.S. Cl. .................. 203/25; 203/53; 203/82; 203/84; 203/DIG. 19; 202/154; 585/810; 585/864
[58] Field of Search .................. 203/53, 60, 58, 62, 203/78, 84, 82, 85, 79, 93, 97, 99, 21, 25, 26, 27, DIG. 19; 202/154; 585/810, 864

[56] References Cited

U.S. PATENT DOCUMENTS

| | | | |
|---|---|---|---|
| 2,600,106 | 6/1952 | Garrett | 203/60 |
| 2,901,404 | 8/1959 | Kirshenbaum et al. | 202/154 |
| 2,971,036 | 2/1961 | James | 203/29 |
| 3,058,893 | 10/1962 | Cahn et al. | 203/84 |
| 3,230,157 | 1/1966 | Hill et al. | 203/53 |
| 3,254,024 | 5/1966 | Huckins et al. | 203/25 |
| 3,378,465 | 4/1968 | Brandt et al. | 203/25 |
| 3,554,873 | 1/1971 | Luther et al. | 203/60 |
| 3,769,217 | 10/1973 | Bannister et al. | 203/60 |
| 3,844,898 | 10/1974 | DeGraff | 202/154 |
| 4,025,398 | 5/1977 | Haselden | 202/154 |
| 4,128,457 | 12/1978 | Barba et al. | 203/53 |
| 4,246,073 | 1/1981 | Umeda et al. | 203/25 |

OTHER PUBLICATIONS

Hydrocarbon Processing, vol. 47, No. 11, pp. 131–134.

Primary Examiner—Wilbur L. Bascomb, Jr.
Attorney, Agent, or Firm—Oblon, Fisher, Spivak, McClelland & Maier

[57] ABSTRACT

In a process for producing butadiene or isoprene having a high purity comprising a step of treating a $C_4$ or $C_5$ hydrocarbon mixture containing butadiene or isoprene by an extractive distillation method in the presence of a selective solvent to obtain crude butadiene or crude isoprene and a step of separating a heavy fraction contained in a small quantity in the thus obtained crude butadiene or crude isoprene by a conventional distillation method in a heavy fraction separating tower, the heat energy can be saved to a great extent by thermally coupling the tower for distilling crude butadiene or crude isoprene used in the above-mentioned extractive-distillation step with the above-mentioned heavy fraction separating tower, namely by feeding a part or the whole of the vapor stream from the top of said tower for distilling crude butadiene or isoprene to said heavy fraction separating tower and feeding a liquid at a rate corresponding to the whole or a part of the reflux rate necessary for the operation of the tower for distilling crude butadiene or crude isoprene, from the heavy fraction separating tower to the tower for distilling crude butadiene or crude isoprene.

19 Claims, 5 Drawing Figures

PROCESS FOR PRODUCING 1,3-BUTADIENE OR 2-METHYL-1,3-BUTADIENE HAVING HIGH PURITY

This invention relates to a process for purifying a $C_4$ or $C_5$ hydrocarbon mixture obtained by naphtha cracking process, dehydrogenation process or the like by an extractive-distillation method with an economized heat energy, thereby producing 1,3-butadiene (hereinafter, simply referred to as butadiene) or 2-methyl-1,3-butadiene (hereinafter, simply referred to as isoprene) having a high purity.

As a process for separating and recovering butadiene or isoprene having a high purity from a $C_4$ or $C_5$ hydrocarbon mixture containing butadiene or isoprene in a high yield, an extractive distillation method is widely known and industrially practised. As the selective solvent for the extractive distillation, polar substances such as acetonitrile, dimethylformamide, N-methylpyrrolidone, furfural, acetone, dimethylacetamide and the like are used.

In Hydrocarbon Processing, Vol. 47, No. 11, pp. 131-134, a one-step extractive distillation process for butadiene using furfural as a selective solvent is disclosed. In this process, the fractions lighter than butadiene are removed in the first extractive distillation step, the crude butadiene containing a small quantity of heavy fraction is distilled out of a solvent stripper and the heavy fraction is removed in the subsequent heavy fraction separating tower to give a high purity butadiene.

In Chem. Techn., 28 Jg., Heft Aug. 8, 1976, pp. 463-466, a two-step process for the extractive distillation of butadiene using dimethylformamide as a selective solvent is disclosed. In this process, the components weaker than butadiene in affinity to the solvent are removed as the light fraction in the first extractive distillation step, the components stronger than butadiene in affinity to the solvent are removed as the heavy fraction in the second extractive distillation step and crude butadiene containing a small quantity of impurity is purified in the subsequent heavy fraction separating tower to give high purity butadiene.

In U.S. Pat. No. 2,971,036, a one-step process for the extractive distillation of isoprene using acetone or acetonitrile as a selective solvent is disclosed. Further, in U.S. Pat. No. 3,230,157, a two-step process for the extractive distillation of isoprene using acetone or acetonitrile as a selective solvent is disclosed.

In all these processes, a light fraction separating tower and/or a heavy fraction separating tower are (is) usually provided for the purpose of further purifying the crude butadiene or the crude isoprene obtained in the extractive distillation step. In the hitherto known techniques, these towers are operated independently of the extractive distillation step.

With the rapid rise of energy cost in the recent years, it is intensely requested to convert the processes to those of energy saving type.

In the hitherto known techniques, and extractive distillation tower or the solvent stripper for distilling out crude butadiene or crude isoprene in the extractive distillation step has a condenser at the top, where the vapor stream is cooled and condensed in order to secure a quantity of reflux necessary for the operation of tower. Since sea water, river water or the like is used as the cooling water for the condensers in economical consideration and from the necessity that the tower must be operated at a pressure as low as possible in order to suppress the polymerization of crude butadiene or crude isoprene, the heat transferred from the top vapor stream to the cooling water in the condenser is disposed without being used effectively at all at the present time. On the other hand, the heavy components contained in a small amount in the crude butadiene or crude isoprene obtained in the extractive distillation step are considerably difficult to remove because their boiling points are very close to that of crude butadiene or crude isoprene, so that a distillation tower having a high plate number and a considerable quantity of reflux are necessitated.

The present inventors have analyzed this tower in detail to find a surprising fact that the minimum quantity of reflux necessary for the separation in this tower is determined by the rectifying section above the feed stage, and the stripping section requires a much smaller quantity of minimum reflux. Thus, the inventors have conducted extensive research on a measure for making the best of this fact to rationalize the process and to save energy. As a result, this object has been achieved by thermally coupling the tower for distilling crude butadiene or crude isoprene in the above-mentioned extractive distillation process with the heavy fraction separating tower.

According to this invention, there is provided a process for producing butadiene or isoprene having a high purity comprising a step of treating a $C_4$ or $C_5$ hydrocarbon mixture containing butadiene or isoprene by an extractive distillation method using a selective solvent to obtain crude butadiene or crude isoprene, and a step of separating the small quantity of heavy fraction contained in said crude butadiene or crude isoprene by a conventional distillation method in a heavy fraction separating tower, characterized by thermally coupling the tower for distilling crude butadiene or crude isoprene used in the extractive distillation step with said heavy fraction separating tower.

In the process of this invention, the term "thermally coupling" means feeding the whole or a part of the top vapor stream of the tower for distilling crude butadiene or crude isoprene into the heavy fraction separating tower without condensing the stream in the condenser and returning a liquid from the latter tower to the former tower in an amount sufficient to secure the quantity of reflux necessary for the operation of the tower for distilling crude butadiene or crude isoprene by said liquid in combination with the reflux from the condenser of said distillation tower. By this measure, the heat quantity removed from the condenser by cooling water can be saved to a great extent. That is, according to this invention, the heat quantity added from the outside of the system can be saved because the heat quantity discarded from the condenser is heat added in any form from the outside of the system. In addition, there are obtained further advantages according to this invention such as saving of cooling water supplied to condenser, reduction of apparatus cost, and so on.

This invention will be explained in detail below referring to the accompanying drawings, in which FIGS. 1-5 illustrate the process for separating butadiene or isoprene of high purity from a $C_4$ or $C_5$ fraction by a extractive distillation process, wherein FIG. 1 is a flow sheet illustrating the hitherto known process and FIGS. 2–5 are flow sheets illustrating embodiments of the process of this invention. In the Figures, the numerals refer to the followings:

Conduit—1, 3, 4, 5, 8, 10, 11, 14, 15, 17, 18, 19, 20, 21, 23, 24, 25, 27, 29, 31, 32, 34, 35, 38, 39, 41, 42, 43, 45, 46, 51, 53, 54, 55, 57, 59, 60, 61, 64, 66, 67, 70, 71, 73, 74, 75, 76, 78, 80, 81, 83, 84, 85, 88, 89

Extractive distillation tower—2, 22, 28, 52,

Solvent stripper—6, 26, 44, 56, 62

Heavy fraction separating tower—12, 36, 68

Tower—77, 86

Reboiler—7, 13, 30, 37, 63, 69, 79, 87

Condenser—9, 16, 33, 40, 65, 72, 82

For simplicity and clarity, most of the pumps, heat exchangers and the like not particularly necessary to explain are omitted in the Figures, and only the main parts are shown. Where some kinds of raw materials are used, a pretreatment step and/or an after-treatment step may be necessary before or after the steps mentioned below, but they are omitted because they are irrelevant to the essence of this invention.

FIG. 1 illustrates the flow scheme of the hitherto known one-step extractive distillation process. A $C_4$ or $C_5$ fraction containing butadiene or isoprene is fed to the middle stage of the extractive distillation tower 2 via the conduit 1. A selective solvent composed of at least one polar solvent is fed to the neighborhood of the top of the tower 2 via the conduit 3. From the top, the components weaker than butadiene or isoprene in affinity to the solvent are discharged via the conduit 4, while the components having a strong affinity to the solvent are discharged together with butadiene or isoprene from the bottom via the conduit 5 and fed to the middle stage of the subsequent solvent stripper 6. The reboiler 7 is provided at the bottom of the solvent stripper 6, while the condenser 9 is provided at the top of the stripper. From the bottom of the solvent stripper 6, the selective solvent separated from hydrocarbons is discharged, and recycled to the extractive distillation tower 2 via the conduit 3. From the top of the tower 6, a vapor composed mainly of crude butadiene or crude isoprene is discharged via the conduit 8, and this stream is condensed by the condenser 9, and a part of the condensate is returned to the solvent stripper 6 as a reflux via the conduit 10 while the remainder is fed to the heavy fraction separating tower 12 via the conduit 11 as a tower top distillate. The heavy fraction separating tower 12 is equipped with the reboiler 13 at the bottom and with the condenser 16 at the top. The small quantity of heavy fraction contained in the crude butadiene or crude isoprene fed via the conduit 11 is discharged from the bottom via the conduit 14. On the other hand, a vapor stream composed mainly of butadiene or isoprene free from the heavy fraction is discharged from the top via the conduit 15 and condensed by the condenser 16, and a part of the condensate is returned to the heavy fraction separating tower 12 via the conduit 17 as a reflux while the remainder is discharged from the system via the conduit 18 as a tower top distillate. This distillate consists essentially of butadiene or isoprene, and is sent to the next step not shown in the figure if the purification thereof is necessary.

Figure 2:
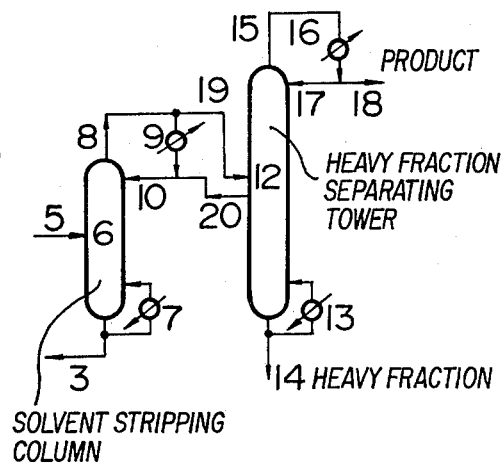

FIG. 2 illustrates the flow scheme of an improved process wherein the solvent stripper 6 and the heavy fraction separating tower 12 are thermally coupled according to this invention. The stream of the vapor discharged from the top of the solvent stripper 6 via the conduit 8 is different from that in the hitherto known processes in that the whole or a part of the vapor stream is fed to the middle stage of the heavy fraction separating tower 12 via the conduit 19 directly without being condensed in the condenser (accordingly, the condenser 9 is unnecessary when the whole of the vapor stream is fed to the heavy fraction separating tower). A part of the liquid flow descending in the heavy fraction separating tower is withdrawn from the middle stage of the tower (preferably from the same stage as the stage to which the conduit 19 is connected or its neighboring stage) via the conduit 20 and fed to the solvent stripper 6 via the conduit 10 either directly or after being joined with a stream from the condenser 9 if it exists. In this case, the operation is controlled so as to secure the same flow rate of liquid as that of the reflux in FIG. 1. While the reflux rate via the conduit 17 should be slightly increased to secure the same separation in the heavy fraction separating tower 12 in the FIG. 2 scheme compared to the FIG. 1 scheme, the degree of this increase, however, is very small as compared with the decrease in amount of condensate in the condenser 9 of the solvent stripper 6. This means that the required energy for the separation can be saved to a great extent according to this invention.

Figure 3:
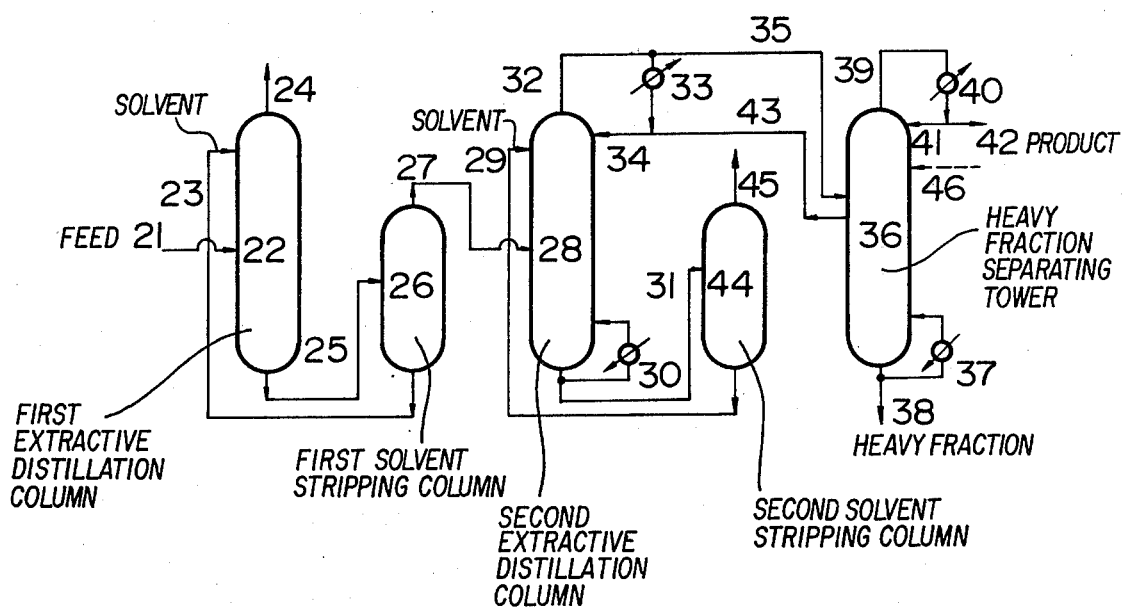

FIG. 3 illustrates the flow scheme where this invention is applied to a two-step extractive distillation process. A $C_4$ or $C_5$ fraction containing butadiene or isoprene is fed to the middle stage of the first extractive distillation tower 22 via the conduit 21. A selective solvent is fed to the neighborhood of the top of the tower 22 via the conduit 23. Components weaker than butadiene or isoprene in affinity to the solvent are discharged from the top via the conduit 24, while components having strong affinity to the solvent are discharged from the bottom via the conduit 25 together with butadiene or isoprene and fed to the middle stage of the subsequent first solvent stripper 26. The solvent free from hydrocarbons is discharged from the bottom of the tower 26 and recycled to the first extractive distillation tower 22 via the conduit 23. Thus, a fraction composed mainly of butadiene or isoprene is discharged from the top of the first solvent stripper 26 via the conduit 27 and fed to the middle stage of the second extractive distillation tower 28. To the neighborhood of the top of the tower 28, the solvent discharged from the bottom of the second solvent stripper 44 is recycled and fed through the conduit 29. The second extractive distillation tower 28 is equipped with the reboiler 30 at the bottom and with the condenser 33 at the top if necessary. From the bottom of the tower 28, a stream comprising a hydrocarbon composed mainly of the components stronger than butadiene or isoprene in affinity to the solvent and the solvent is discharged via the conduit 31, and sent to the middle stage of the second solvent stripper 44. A stream of hydrocarbon is discharged from the system at the top of the tower 44 via the conduit 45, while the solvent free from hydrocarbon is discharged from the bottom and recycled to the second extractive distillation tower 28 via the conduit 29. On the other hand, the whole or a part of the vapor stream composed mainly of crude butadiene or crude isoprene, discharged from the top of the tower 28 via the conduit 32, is fed to the middle stage of the heavy fraction separating tower 36 via the conduit 35 directly without being condensed in the condenser 33 (accordingly, the condenser 33 is unnecessary when the whole of the vapor stream is fed to the tower 36). From the middle stage of the heavy fraction separating tower 36, a part of the liquid flow descending in the tower is withdrawn via the conduit 43 and then fed via the conduit 34 as a reflux to the top of the second extractive distillation tower 28 either directly or after being joined with the reflux from the condenser 33 if it exists. Explanation of the heavy fraction separating tower 36 is omitted here because it is the same as the explanations of the heavy fraction separating towers in FIGS. 1 and 2.

Figure 4:
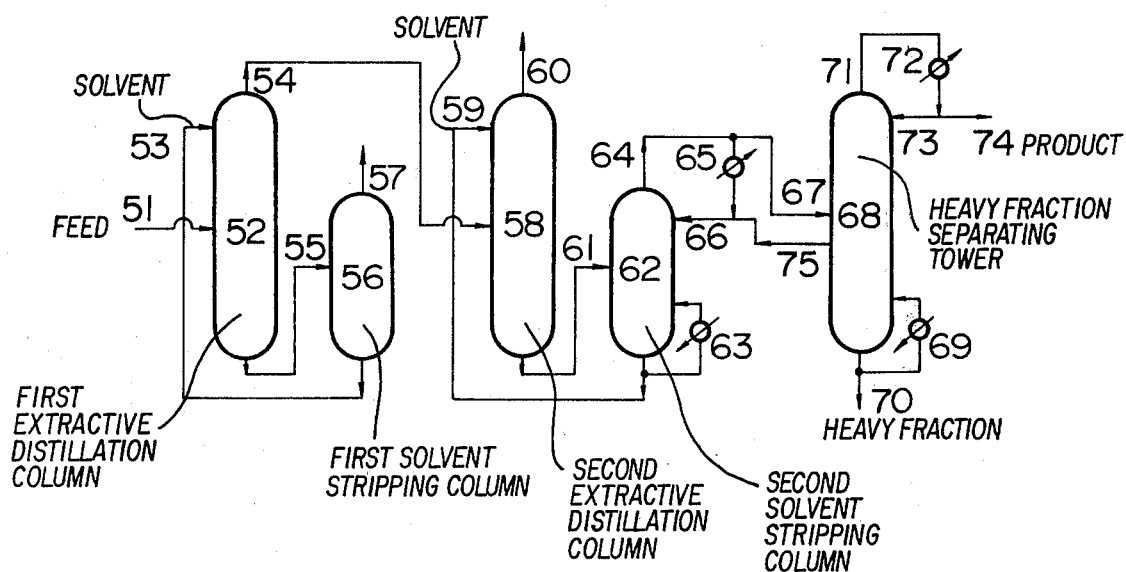

FIG. 4 illustrates the flow scheme where this invention is applied to another two-step extractive distillation process. In this flow scheme, the first extractive distillation step comprising the first extractive distillation tower 52 and the first solvent stripper 56 is for removing the components stronger than butadiene or isoprene in affinity to the solvent (the components are discharged from the system via the conduit 57), while the second extractive distillation step comprising the second extractive distillation tower 58 and the second solvent stripper 62 is for removing the components weaker than butadiene or isoprene in affinity to the solvent (the components are discharged from the system via the conduit 60), and the crude butadiene or crude isoprene is obtained as a tower top component of the tower 62. In this flow scheme, accordingly, it will be easily understood that the anode of thermal coupling between the second solvent stripper 62 and the heavy fraction separator tower 68 is just the same as in FIG. 2.

In FIGS. 2-4, the difference between the quantity of vapor streams 19, 35 or 67 fed to the heavy fraction separating tower 12, 36 or 68 and the quantity of liquid stream 20, 43 or 75 from said tower 12, 36 or 68 corresponds to the feed rate to the heavy fraction separating tower in the hitherto known processes. Therefore, the feeding points and withdrawing points for these flows are usually positioned on the same stage, though there is no problem practically so far as they are provided on the stages near one another.

Figure 5:
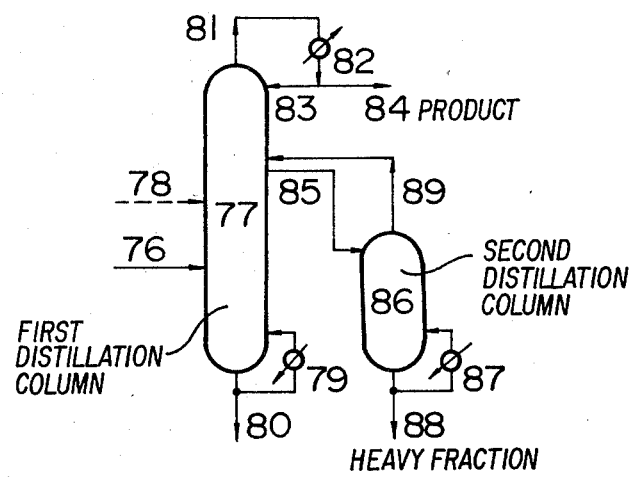

FIG. 5 illustrates another embodiment of this invention. In this scheme, solvent stripper or extractive distillation tower and heavy fraction separating tower are thermally coupled to each other in a different way from FIGS. 2-4. The tower 77 is a unification of the towers to be thermally coupled in the extractive distillation step in FIGS. 2-4 and the rectifying section of a heavy fraction separating tower, and the tower 86 is composed only of the stripping section of the heavy fraction separating tower. To the tower 77 is supplied the feed via the conduit 76 (corresponding to the conduits 5, 27 and 61 in FIGS. 2 to 4) and the circulating solvent is fed via the conduit 78 (only in the case corresponding to FIG. 3). From the top of the tower 77, a stream of purified butadiene or isoprene is discharged out of the system via the conduit 84 (corresponding to the conduits 18, 42 and 74 in FIGS. 2 to 4). A part of the liquid descending in the tower 77 is withdrawn from the middle stage above the conduits 76 and 78 of the tower 77 via the conduit 85 and fed to the top stage of the tower 86. A part of this liquid is discharged out of the system from the bottom via the conduit 88 as a heavy fraction, while the remainder is heated in the reboiler 87 and returned from the top of the tower 86 via the conduit 89 to the tower 77 as a vapor stream. Though the position at which the conduit 89 is connected to the tower 77 is preferably at the same stage as the position at which the conduit 85 is connected, there is no problem practically so far as they are at neighboring stages.

It is preferred that substantially no selective solvent be contained in the stream 19, 35, 67 or 85 fed to the heavy fraction separating tower, because the excessive selective solvent if any acts so as to disturb the separation of the crude butadiene or crude isoprene from the heavy olefins in the heavy fraction separating tower. In the case of light solvents such as acetonitrile or acetone, it is sometimes difficult to satisfy the above-mentioned conditions. In such a case, the problem can be coped with by, for example, providing, on the way of the flow to the heavy fraction separating tower, a step of washing with water by such a method as not to cause phase change of the vapor stream. As another method, it can also be coped with by withdrawing the whole liquid from the middle stage of the tower, feeding a part thereof to the extractive distillation step, washing the remaining liquid flow with water to remove the selective solvent, and then returning it to the heavy fraction separating tower because it is mainly at the stripping section that the existence of the selective solvent would affect adversely the separation of heavy olefins from butadiene or isoprene in the heavy fraction separating tower.

This invention will be explained below in more detail referring to Examples, which are not by way of limitation but by way of illustration.

EXAMPLE 1

Isoprene was purified along the flow scheme of FIG. 3 by using a solvent mixture consisting of acetonitrile and water. Though it is not shown in the Figure, the raw $C_5$ fraction was previously heat-treated to dimerize the major part of cyclopentadiene, and then it was treated in a preliminary concentration tower to separate the heavy fraction and concentrate isoprene to some extent. The fraction thus obtained was fed to the first extractive distillation step via the conduit 21 and the concentrated isoprene stream which was obtained as the overhead product of the first solvent stripper 26 via conduit 27 was fed to the second extractive distillation tower 28. The operating conditions of the tower 28 and the tower 36 were as follows:

|  | Tower 28 | Tower 36 |
| --- | --- | --- |
| Total number of plates | 110 | 110 |
| Raw material feed point (counted from the bottom) | 40th plate | 50th plate |
| Solvent feed point (counted from the bottom) | 104th plate | — |
| Top pressure (kg/cm$^2$ G) | 1.0 | 0.2 |
| top temperature (°C.) | 54 | 41 |
| Bottom temperature (°C.) | 102 | 50 |
| Reflux ratio | (3.0) | 6.2 |

The flow rates in the main conduits were as follows:

|  | (Unit: kg/hr) | |
| --- | --- | --- |
|  | conduit 27 | conduit 42 |
| 1,4-Pentadiene | 256 | 256 |
| 2-Butyne | 187 |  |
| 1-Pentene | 21 | 21 |
| 2-Methyl-1-butene |  |  |
| 2-Methyl-1-buten-3-yne | 26 | 60 ppm |
| Isoprene | 4,292 | 4,240 |
| 2-Pentene | 24 | 24 |
| 2-Methyl-2-butene |  |  |
| 1,3-Pentadiene | 38 | 50 ppm |
| 1-Pentyne | 12 | — |

|  | (Unit: kg/hr) | |
| --- | --- | --- |
|  | conduit 27 | conduit 42 |
| Cyclopentadiene | 84 | 0.5 ppm |
| Acetonitrile | 133 | — |
| Water | 14 | 1 |
| Total | 5087 | 4640.5 |

Conduit 39: 24,700 kg/hr
Conduit 31: 24,877 kg/hr
Conduit 35: 19,640 kg/hr
Conduit 38: 593 kg/hr
Conduit 43: 14,730 kg/hr (=Conduit 34)
Conduit 45: 179 kg/hr
Conduit 46: 400 kg/hr Condenser 33 was not used. Water was fed to the top stage of the tower 36 by means of the conduit 46 in order to wash the acetonitrile coming into the system via the conduit 35. The acetonitrile removed by the water washing was separated as an aqueous phase from the hydrocarbon and withdrawn from the bottom (in FIG. 3, it is summarized in the conduit 38). In this case, the quantities of heat added to the reboilers 30 and 37 were as follows:

Reboiler 30: $1,970 \times 10^3$ Kcal/hr
Reboiler 37: $1,130 \times 10^3$ Kcal/hr

COMPARATIVE EXAMPLE 1

In Example 1, the operation was carried out by the hitherto known process. That is, without thermally coupling the extractive distillation tower 28 and the heavy fraction separating tower 36, the top vapor stream of the tower 28 was wholly condensed in the condenser 33, and it was partially returned to the tower 28 as a reflux (reflux ratio=3.0) and the remainder was fed to the tower 36 in the liquid state. A reflux ratio of 6.0 was necessary for realizing the same separation in the tower 36 as in Example 1. In this case, the quantities of heat added to the reboilers 30 and 37 were as follows.

Reboiler 30: $1,970 \times 10^3$ Kcal/hr
Reboiler 37: $2,820 \times 10^3$ Kcal/hr By comparing these values with those in Example 1, it is apparent that the quantity of heat necessary for the operation of the tower 36 could be reduced to 40% by this invention, as compared with hitherto known process.

EXAMPLE 2

Butadiene was purified by using a solvent mixture consisting of acetonitrile and water according to the process of this invention wherein the solvent stripper 6 and the heavy fraction separating tower 12 were thermally coupled along the flow scheme in FIG. 2. In this case, the condenser 9 was not used. For obtaining, from the conduit 18, butadiene having the same purity as in the hitherto known process wherein the solvent stripper 6 and the heavy fraction separating tower 12 are not thermally coupled (the flow is the same as in FIG. 1 and the condenser 9 is used), the flow rates in the conduits 3, 5, 8, 10, 14 and 18 were the same in both cases, but the flow rate (reflux rate) in the conduit 17 had to be increased by 10%. Although the heat duty in the reboiler 7 was the same in both cases at this time, the heat duty in the reboiler 13 was reduced to 49% according to the process of this invention, as compared with that in the hitherto known process.

EXAMPLE 3

Butadiene was purified along the flow scheme of FIG. 3 by using a solvent mixture consisting of acetonitrile and water according to the process of this invention in which the second extractive distillation tower 28 and the heavy fraction separating tower 36 were thermally coupled.

The operating conditions of the tower 28 and the tower 36 were as follows:

|  | Tower 28 | Tower 36 |
| --- | --- | --- |
| Total number of plates | 130 | 100 |
| Raw material feed point (counted from the bottom) | 15th plate | 50th plate |
| Solvent feed point (counted from the bottom) | 110th plate | — |
| Top pressure (kg/cm² G) | 3.8 | 2.9 |
| Top temperature (°C.) | 41 | 36 |
| Bottom temperature (°C.) | 131 | 50 |
| Reflux ratio | (2.8) | 5.1 |

The flow rates in the main conduits were as follows:

|  | (Unit: kg/hr) | |
| --- | --- | --- |
|  | conduit 27 | conduit 42 |
| i-Butene | 8 | 8 |
| 1-Butene |  |  |
| Trans-2-butene | 34 | 25 |
| Cis-2-butene | 332 | 32 |
| 1,3-Butadiene | 12,397 | 12,263 |
| 1,2-Butadiene | 41 | 10 ppm |
| Methylacetylene | 146 | 146 |
| Ethylacetylene | 41 | 16 ppm |
| Vinylacetylene | 162 | 24 ppm |
| Acetonitrile | 4 | — |
| Water | 26 | 12 |
| Total | 13,191 | 12,486 |

Conduit 29: 21,224 kg/hr
Conduit 31: 21,673 kg/hr
Conduit 35: 48,420 kg/hr
Conduit 38: 256 kg/hr
Conduit 43: 35,678 kg/hr
Conduit 45: 445 kg/hr In this Example, the condenser 33 was not used, and the quantities of heat added to the reboilers 30 and 37 were as follows:

Reboiler 30: $5,030 \times 10^3$ Kcal/hr
Reboiler 37: $2,530 \times 10^3$ Kcal/hr

COMPARATIVE EXAMPLE 3

In Example 3, the operation was carried out by the hitherto known process. That is, without thermally coupling the extractive distillation tower 28 and the heavy fraction separating tower 36, the top vapor stream of the tower 28 was wholly condensed in the condenser 33, and it was partially returned to the tower 28 as a reflux (reflux ratio=2.8), and the remainder was fed to the tower 36 in the liquid state. A reflux ratio of 4.6 was necessary for realizing the same separation in the tower 36 as in Example 3. In this case, the quantities of heat added to the reboilers 30 and 37 were as follows:

Reboiler 30: $5,030 \times 10^3$ Kcal/hr
Reboiler 37: $6,400 \times 10^3$ Kcal/hr By comparing these values with those in Example 3, it is apparent that the quantity of heat necessary for the operation of the tower 36 could be reduced to 40% by this invention, as compared with the hitherto known process.

What is claimed is:

1. A process for producing high purity butadiene or isoprene comprising treating a $C_4$ or $C_5$ hydrocarbon mixture containing butadiene or isoprene by an extractive distillation method, comprising at least one extractive distillation step and at least one solvent-stripping step, in the presence of a selective solvent to obtain crude butadiene or crude isoprene containing a small quantity of heavy fraction; and separating said heavy fraction from said crude butadiene or crude isoprene in a heavy fraction separating tower, wherein said crude butadiene or crude isoprene is taken out of the top of a column as a top vapor in the extractive distillation step or the solvent-stripping step, at least a part thereof is fed to the middle stage of said heavy fraction separating tower, the remainder is condensed and refluxed to said column, and a liquid is withdrawn from said middle stage or its neighboring stage of said heavy fraction separating tower and then fed to said column together with said remainder, the total flow rate of said liquid and said remainder corresponding to the reflux rate necessary to operate said column.

2. A process according to claim 1, wherein said heavy fraction separating tower comprises a rectifying section and a stripping section, and said rectifying section is unified with said column and said liquid from the middle stage of said unified tower is withdrawn and fed to said stripping section, and top vapor stream of said stripping section is returned to said unified tower.

3. A process according to claim 1 or 2, wherein extractive distillation is effected by a one-step extractive distillation process and said column functions as a solvent stripper.

4. A process according to claim 1 or 2, wherein extractive distillation is effected by a two-step extractive distillation process by which fractions lighter than butadiene or isoprene are separated in a first step and fractions heavier than butadiene or isoprene are separated in a second step, and said column acts as a second extractive distillation tower in the second step of said two-step extractive distillation process.

5. A process according to claim 1 or 2, wherein said extractive distillation is effected by a two-step extractive distillation process by which fractions heavier than butadiene or isoprene butadiene are separated by means of a first extractive distillation tower and a first solvent stripper as a first step and fractions lighter than butadiene or isoprene butadiene are separated by means of a second extractive distillation tower and a second solvent stripper as a second step, and said column acts as a second solvent stripper.

6. A process according to claim 1, wherein thermal energy is transferred by feeding the whole of the top vapor stream from said column to said heavy fraction separating tower, and feeding a liquid from said heavy fraction separating tower to said column at a rate corresponding to reflux rate necessary to the operation of said column.

7. A process for producing high purity butadiene or isoprene comprising:

feeding a $C_4$ or $C_5$ hydrocarbon mixture containing butadiene or isoprene to the middle section of an extractive distillation column;

feeding a selective solvent to the upper section of said extractive distillation column;

from the top of said extractive distillation column, withdrawing a stream of components weaker than buadiene or isoprene in affinity to said selective solvent;

from the bottom of said extractive distillation column, withdrawing a liquid stream comprising selective solvent, components stronger than butadiene or isoprene in affinity to said selective solvent and butadiene or isoprene, and feeding said liquid stream to the middle section of a solvent stripping column;

from the bottom of said solvent stripper column, withdrawing a liquid stream of said selective solvent and recycling a portion of the same to the upper section of said extractive distillation column, the remaining portion passing through a reboiler and being returned to the bottom of the column as vapor;

from the top of said solvent stripping column, withdrawing a vapor stream comprising crude butadiene or crude isoprene containing a small quantity of heavy fraction and feeding at least a portion of the vapor stream to the middle section of a heavy fraction separating tower, the remaining portion of the vapor stream being condensed and returned to the upper section of said solvent stripping column;

from the middle section of said heavy fraction separating tower, withdrawing a portion of the liquid flow descending the tower and feeding the liquid to the upper section of said solvent stripping column, the total flow rate of this liquid and the condensed vapor returned to the upper section of said solvent stripping column corresponding to the reflux rate necessary to operate said solvent stripping column;

from the top of the heavy fraction separating tower, withdrawing a vapor stream comprising butadiene or isoprene free from heavy fraction, condensing the vapor stream, returning a portion of the condensate to the tower as reflux and withdrawing a portion as product;

from the bottom of the heavy fraction separating tower, withdrawing a liquid stream comprising said heavy fraction from said tower and returning only a portion of said liquid stream to said tower as a vapor after passage through a reboiler.

8. The process according to claim 7, wherein all of the vapor stream withdrawn from the top of said solvent stripping column is fed to the middle section of the heavy fraction separating tower and the liquid withdrawn from the middle section of the heavy fraction separating tower supplies the reflux necessary to operate said solvent stripping column.

9. The process according to claim 7, wherein the vapor stream withdrawn from the top of said solvent stripping column is fed to the heavy fraction separating tower at the same stage at which liquid is withdrawn from the heavy fraction separating tower for feed to the upper section of said solvent stripping column.

10. A process for producing high purity butadiene or isoprene comprising:

feeding a $C_4$ or $C_5$ hydrocarbon mixture containing butadiene or isoprene to the middle section of a first extractive distillation column;

feeding a selective solvent to the upper section of said first extractive distillation column;

from the top of said first extractive distillation column, withdrawing a stream of components weaker than butadiene or isoprene in affinity to said selective solvent;

from the bottom of said first extractive distillation column, withdrawing a liquid stream comprising selective solvent, components stronger than butadiene or isoprene in affinity to said selective solvent and butadiene or isoprene, and feeding said liquid stream to the middle section of a first solvent stripping column;

from the bottom of said first solvent stripping column, withdrawing a liquid stream of said selective solvent and recycling the same to the upper section of said first extractive distillation column;

from the top of said first solvent stripping column, withdrawing a vapor stream composed mainly of butadiene or isoprene and feeding said vapor stream to the middle section of a second extractive distillation column;

feeding a selective solvent to the upper section of said second extractive distillation column;

from the bottom of said second extractive distillation column, withdrawing a liquid stream comprising selective solvent and component stronger than butadiene or isoprene in affinity to said selective solvent, recycling a portion of this liquid stream to the bottom of said second extractive distillation column as vapor after passage through a reboiler and feeding the remaining portion of said liquid to the middle section of a second solvent stripping column;

from the top of said second solvent stripper column, withdrawing a vapor stream comprising components stronger than butadiene or isoprene in affinity to said selective solvent;

from the bottom of said second solvent stripping column, withdrawing a liquid stream of said selective solvent and recycling the same to the upper section of said second extractive distillation column;

from the top of said second extractive distillation column, withdrawing a vapor stream comprising crude butadiene or crude isoprene containing a small quantity of heavy fraction and feeding at least a portion of the vapor stream to the middle section of a heavy fraction separating tower, the remaining portion of the vapor stream being condensed and returned to the upper section of said second extractive distillation column;

from the middle section of said heavy fraction separating tower, withdrawing a portion of the liquid flow descending the tower and feeding the liquid to the upper section of said second extractive distillation column, the total flow rate of this liquid and the condensed vapor stream returned to the upper section of said second extractive distillation column corresponding to the reflux rate necessary to operate said second extractive distillation column;

from the top of the heavy fraction separating tower, withdrawing a vapor stream comprising butadiene or isoprene free from heavy fraction, condensing the vapor stream, returning a portion of the condensate to the tower as reflux and withdrawing a portion as product;

from the bottom of the heavy fraction separating tower, withdrawing a liquid stream comprising said heavy fraction from said tower and returning only a portion of said liquid stream of said tower as vapor after passage through a reboiler.

11. The process according to claim 10, wherein all of the vapor stream withdrawn from the top of said second extractive distillation column is fed to the middle section of the heavy fraction separating tower and the liquid withdrawn from the middle section of the heavy fraction separating tower supplies the reflux necessary to operate said second extractive distillation column.

12. The process according to claim 10, wherein the vapor stream withdrawn from the top of said second extractive distillation column is fed to the heavy fraction separating tower at the same stage at which liquid is withdrawn from the heavy fraction separating tower for feed to the upper section of said second extractive distillation column.

13. The process according to claim 10, further comprising: feeding water to the upper section of said heavy fraction separating tower, whereby any selective solvent remaining in the vapor stream coming from the top of the second extractive distillation column is removed as an aqueous phase in the liquid stream withdrawn from the bottom of said heavy fraction separating tower.

14. A process for producing high purity butadiene or isoprene comprising:

feeding a $C_4$ or $C_5$ hydrocarbon mixture containing butadiene or isoprene to the middle section of a first extractive distillation column;

feeding a selective solvent to the upper section of said first extractive distillation column;

from the bottom of said first extractive distillation column, withdrawing a liquid stream comprising selective solvent and components stronger than butadiene or isoprene in affinity to said selective solvent, and feeding said liquid stream to the middle section of a first solvent stripping column;

from the top of said first solvent stripping column, withdrawing a vapor stream comprising components stronger than butadiene or isoprene in affinity to said selective solvent;

from the bottom of said first solvent stripping column, withdrawing a liquid stream of said selective solvent and recycling the same to the upper section of said first extractive distillation column;

from the top of said first extractive distillation column, withdrawing a vapor stream comprising components weaker than butadiene or isoprene in affinity to the selective solvent and butadiene or isoprene and feeding said vapor stream to the middle section of a second extractive distillation column;

feeding selective solvent to the upper section of said second extractive distillation column;

from the top of said second extractive distillation column, withdrawing a vapor stream comprising components weaker than butadiene or isoprene in affinity to said selective solvent;

from the bottom of said second extractive distillation column, withdrawing a liquid stream comprising selective solvent and butadiene or isoprene, and feeding said liquid stream to the middle section of a second solvent stripping column;

from the bottom of said second solvent stripping column, withdrawing a liquid stream of said selective solvent, recycling a portion of this liquid stream to the bottom of said second solvent stripping column as vapor after passage through a reboiler and recycling the remaining portion of said liquid to the upper section of said second extractive distillation column;

from the top of said second solvent stripping column, withdrawing a vapor stream comprising crude butadiene or crude isoprene containing a small quantity of heavy fraction and feeding at least a portion of the vapor stream to the middle section of a heavy fraction separating tower, the remaining portion of the vapor stream being condensed and returned to the upper section of said second solvent stripping column;

from the middle section of said heavy fraction separating tower, withdrawing a portion of the liquid flow descending the tower and feeding the liquid to the upper section of said solvent stripping column, the total flow of this liquid and the condensed vapor stream returned to the upper section of said second solvent stripping column corresponding to the reflux rate necessary to operate said second solvent stripping column;

from the top of said heavy fraction separating tower, withdrawing vapor stream comprising butadiene or isoprene free from heavy fraction, condensing the vapor stream, returning a portion of the condensate to the tower as reflux and withdrawing a portion as product;

from the bottom of the heavy fraction separating tower, withdrawing a liquid stream comprising said heavy fraction from said tower and returning only a portion of said liquid stream to said tower as vapor after passage through a reboiler.

15. The process according to claim 14, wherein all of the vapor stream withdrawn from the top of said second solvent stripping column is fed to the middle section of the heavy fraction separating tower and the liquid withdrawn from the middle section of the heavy fraction separating tower supplies the reflux necessary to operate said second solvent stripping column.

16. The process according to claim 14, wherein the vapor stream withdrawn from the top of said second solvent stripping column is fed to the heavy fraction separating tower at the same stage at which liquid is withdrawn from the heavy fraction separating tower for feed to the upper section of said second solvent stripping column.

17. A process for producing high purity butadiene or isoprene comprising:

feeding a $C_4$ or $C_5$ hydrocarbon mixture containing butadiene or isoprene to the middle section of an extractive distillation column;

feeding a selective solvent to the upper section of said extractive distillation column;

from the top of said extractive distillation column, withdrawing a vapor stream of components weaker than butadiene or isoprene in affinity to said selective solvent;

from the bottom of said extractive distillation column, withdrawing a liquid stream comprising selective solvent, components stronger than butadiene or isoprene in affinity to said selective solvent and butadiene or isoprene, and feeding said liquid stream to the middle section of a first distillation column;

from the bottom of said first distillation column, withdrawing a liquid stream of selective solvent, recycling a portion of said selective solvent to the upper section of said extractive distillation column and returning a portion of said selective solvent to the bottom section of said first distillation column, as vapor, after passage through a reboiler;

from the middle section of said first distillation column, at a point above the inlet for the liquid stream from the bottom for the extractive distillation column, withdrawing a portion of the liquid descending the first distillation column, and feeding said liquid stream to the upper section of a second distillation column;

from the bottom of said second distillation column, withdrawing a liquid stream of heavy fraction from said second distillation column and returning only a portion of said liquid stream to the bottom section of said second distillation column, as vapor, after passage through a reboiler;

from the top of said second distillation column, withdrawing a vapor stream and feeding said vapor stream to the middle section of said first distillation column at about the stage where the liquid stream for feed to the second distillation column is withdrawn;

from the top of the first distillation column, withdrawing a vapor stream of purified butadiene or isoprene, condensing the vapor stream, returning a portion of the condensate to the top of said first distillation column as reflux and withdrawing a portion of the condensate as product.

18. A process for producing high purity butadiene or isoprene comprising:

feeding a $C_4$ or $C_5$ hydrocarbon mixture containing butadiene or isoprene to the middle section of an extractive distillation column;

feeding a selective solvent to the upper section of said extractive distillation column;

from the top of said extractive distillation column, withdrawing a vapor stream of components weaker than butadiene or isoprene in affinity to said selective solvent;

from the bottom of said extractive distillation column, withdrawing a liquid stream comprising selective solvent, components stronger than butadiene or isoprene in affinity to said selective solvent and butadiene or isoprene, and feeding said liquid stream to the middle section of a solvent stripping column;

from the bottom of said solvent stripping column, withdrawing a liquid stream of selective solvent and recycling said stream to the upper section of said extractive distillation column;

from the top of said solvent stripping column, withdrawing a vapor stream composed mainly of butadiene or isoprene and feeding said vapor stream to the middle section of a first distillation column;

feeding a selective solvent to the middle section of said first distillation column, at a point above the inlet for said vapor stream from the solvent stripping column;

from the bottom of said first distillation column, withdrawing a liquid stream of selective solvent, returning a portion of said selective solvent to the bottom section of said first distillation column as a vapor after passage through a reboiler and recycling the remaining liquid portion of selective solvent to the middle section of said first distillation column, after removing the components stronger than butadiene or isoprene in affinity to the selective solvent;

from the middle section of said first distillation column, at a point above the selective solvent inlet, withdrawing a portion of the liquid descending said column and feeding said liquid stream to the upper section of a second distillation column;

from the bottom of said second distillation column, withdrawing a liquid stream of heavy fraction from said second distillation column and returning only a portion of said liquid stream to the bottom section of said second distillation column as a vapor after passage through a reboiler;

from the top of said second distillation column, withdrawing a vapor stream and feeding said vapor stream to the middle section of said first distillation column at about the stage where the liquid stream for feed to the second distillation column is withdrawn;

from the top of the first distillation column, withdrawing a vapor stream of purified butadiene or isoprene, condensing the vapor stream, returning a portion of the condensate to the top of said first distillation column as reflux and withdrawing a portion of the condensate as product.

19. A process for producing high purity butadiene or isoprene comprising:

feeding a $C_4$ or $C_5$ hydrocarbon mixture containing butadiene or isoprene to the middle section of a first extractive distillation column;

feeding a selective solvent to the upper section of said first extractive distillation column;

from the bottom of said first extractive distillation column, withdrawing a liquid stream comprising selective solvent and components stronger than butadiene or isoprene in affinity to said selective solvent, and feeding said liquid stream to the middle section of a solvent stripping column;

from the top of said solvent stripping column, withdrawing a vapor stream comprising components stronger than butadiene or isoprene in affinity to said selective solvent;

from the bottom of said solvent stripping column, withdrawing a liquid stream of selective solvent and recycling the same to the upper section of said first extractive distillation column;

from the top of said first extractive distillation column, withdrawing a vapor stream comprising components weaker than butadiene or isoprene in affinity to the selective solvent and butadiene or isoprene and feeding said vapor stream to the middle section of a second extractive distillation column;

feeding selective solvent to the upper section of said second extractive distillation column;

from the top of said second extractive distillation column, withdrawing a vapor stream comprising components weaker than butadiene or isoprene in affinity to said selective solvent;

from the bottom of said second extractive distillation column, withdrawing a liquid stream comprising selective solvent and butadiene or isoprene, and feeding said liquid stream to the middle section of a first distillation column;

from the bottom of said first distillation column, withdrawing a liquid stream of selective solvent, recycling a portion of said selective solvent to the upper section of said second extractive distillation column and returning a portion of said selective solvent to the bottom section of said first distillation column, as vapor, after passage through a reboiler;

from the middle section of said first distillation column, at a point above the inlet for the liquid stream from the bottom of the second extractive distillation column, withdrawing a portion of the liquid descending the first distillation column, and feeding said liquid stream to the upper section of a second distillation column;

from the bottom of said second distillation column, withdrawing a liquid stream of heavy fraction from said second distillation column and returning only a portion of said liquid stream to the bottom section of said second distillation column, as vapor, after passage through a reboiler;

from the top of said second distillation column, withdrawing a vapor stream and feeding said vapor stream to the middle section of said first distillation column at about the stage where the liquid stream for feed to the second distillation column is withdrawn;

from the top of the first distillation column, withdrawing a vapor stream of purified butadiene or isoprene, condensing the vapor stream, returning a portion of the condensate to the top of said first distillation column as reflux and withdrawing a portion of the condensate as product.

* * * * *